United States Patent
Klingenbeck-Regn et al.

(10) Patent No.: US 6,173,033 B1
(45) Date of Patent: Jan. 9, 2001

(54) X-RAY COMPUTED TOMOGRAPHY APPARATUS FOR PRODUCING X-RAY SHADOWGRAPHS

(75) Inventors: Klaus Klingenbeck-Regn, Nuremberg; Guenter Dehner, Erlangen, both of (DE)

(73) Assignee: Siemens Aktiengesellschaft, Munich (DE)

( * ) Notice: Under 35 U.S.C. 154(b), the term of this patent shall be extended for 0 days.

(21) Appl. No.: 09/083,513

(22) Filed: May 22, 1998

(30) Foreign Application Priority Data

May 22, 1997 (DE) .............................................. 197 21 535

(51) Int. Cl.[7] ...................................................... A61B 6/00
(52) U.S. Cl. ................................ 378/20; 378/10; 378/19; 378/146
(58) Field of Search ................................ 378/10, 19, 20, 378/145, 146

(56) References Cited

U.S. PATENT DOCUMENTS

| | | | |
|---|---|---|---|
| 4,160,167 | * 7/1979 | Weiss et al. | 378/19 |
| 4,176,280 | * 11/1979 | Greschat et al. | 378/19 |
| 4,187,430 | * 2/1980 | Schmidt | 378/19 |
| 4,193,001 | * 3/1980 | Liebetruth | 378/19 |
| 4,324,978 | * 4/1982 | Kalender et al. | 250/445 |
| 4,352,986 | * 10/1982 | Pfeiler | 378/14 |
| 4,477,922 | * 10/1984 | Liebetruth | 378/20 |
| 4,995,107 | * 2/1991 | Klingenbeck | 378/7 |
| 5,291,402 | * 3/1994 | Pfoh | 378/13 |
| 5,315,628 | * 5/1994 | Guendel | 378/20 |
| 5,373,543 | * 12/1994 | Ackermann et al. | 378/20 |
| 5,377,250 | * 12/1994 | Hu | 378/15 |
| 5,386,446 | * 1/1995 | Fujimoto et al. | 378/20 |
| 5,430,783 | * 7/1995 | Hu et al. | 378/15 |
| 5,430,784 | * 7/1995 | Ribner et al. | 378/19 |
| 5,583,903 | * 12/1996 | Saito et al. | 378/19 |
| 5,592,523 | * 1/1997 | Tuy et al. | 378/19 |
| 5,684,855 | * 11/1997 | Aradate et al. | 378/4 |

* cited by examiner

Primary Examiner—David P. Porta
Assistant Examiner—Allen C. Ho
(74) Attorney, Agent, or Firm—Hill & Simpson (57) ABSTRACT

An X-ray computed tomography apparatus having a two-dimensional detector allows X-ray shadowgraphs to be alternatively produced with using one or several detector rows. For this purpose, a slot diaphragm near the tube and a slot diaphragm near the detector are provided. For the superposition of the shadowgraphs of the individual detector rows, an on-line computing method is used that includes a deblurring filter for the reduction of image blurring due to table motion, and a method for scatter radiation correction in a multirow or matrix detector.

28 Claims, 9 Drawing Sheets

X-RAY COMPUTED TOMOGRAPHY APPARATUS FOR PRODUCING X-RAY SHADOWGRAPHS

BACKGROUND OF THE INVENTION

1. Field of the Invention

The present invention is directed to an X-ray computer tomography apparatus of the type which is capable of producing an X-ray shadowgraph, in addition to a computed tomogram.

2. Description of the Prior Art

X-ray computed tomography apparatuses are known in which the X-ray source emits a fan-shaped X-ray beam that strikes a detector row constructed from a series of detector elements. For the production of computed tomograms, the measurement arrangement of the X-ray source and the detector rows is rotated around a system axis. From the detector output signals, produced in various projections, a computer calculates an image of the transirradiated region of the patient.

For the production of overview exposures, namely X-ray shadowgraphs, it is known from U.S. Pat. No. 4,477,922 to lock the measurement arrangement against rotation in such a computed tomography apparatus, and to carry out a relative movement between the measurement arrangement and the patient table, or at least the slab of the table, in the direction of the system axis, e.g. by displacing the patient table (or slab). The path of movement of the patient table thereby corresponds essentially to the length of the X-ray shadowgraph. Depending on the integration time of the data acquisition system, the data of a number of projections can be combined to form a line of the X-ray shadowgraph. In conventional systems, the resolution in the X-ray shadowgraph in the direction of the system axis is determined essentially by the slice collimation used for the exposure.

For the representation of the shadowgraph, the data recorded with the data acquisition system are A/D converted and transferred to a central processor. In the central processor, a normalization of the data dependent on the measurement system is conducted, the measured radiation intensities are converted to attenuation values and a sliding combination, dependent on the speed of the movement of the measurement system relative to the patient, of the projections (measured at fixed time intervals) of attenuation values is undertaken to form equidistant image lines of the shadowgraph. In a further step, the shadowgraph (obtained in a cylindrical projection) is reformatted into a flat image, with pixels that are likewise equidistant in the transverse direction. A two-dimensional development of the shadowgraph, for increasing the image contrast, with simultaneous contour enhancement. follows the construction of the image. The two-dimensional filtering can take place either in a separate calculation step or on-line. corresponding to U.S. Pat. No. 5,315,628, i.e. in parallel with the data acquisition.

It is also known to expose an X-ray shadowgraph using a matrix detector, as described in U.S. Pat. No. 4,352,986, which is constructed from a series of parallel detector rows. If the matrix detector covers the entire region of examination, a relative motion between the measurement arrangement and the patient table can be avoided.

SUMMARY OF THE INVENTION

An object of the present invention is to provide an X-ray computed tomography apparatus with a matrix detector or multirow detector wherein, besides the production of tomograms, X-ray shadowgraphs can alternatively be produced using a row of detectors or using several detector rows.

Typically, "several detector rows" designates any arrangement having a number of detector rows greater than one. The arrangement thus includes a matrix detector (array detector). The region of examination of the patient can be equal to or greater than the surface covered by the detector system.

This object is achieved according to the invention in an X-ray computed tomography apparatus having a diaphragm arrangement with a diaphragm near the tube and a diaphragm near the detector, so that, alternatively, one detector row or several detector rows can be selected from the matrix detector for use in detecting radiation, depending on whether a tomogram (one row) or a shadowgraph (multiple rows) is to be produced.

If more than one row is selected during the data acquisition, and the patient is simultaneously moved relative to the measurement system, the patient is scanned several times in chronologically displaced fashion, in a manner corresponding to the number of detector rows used. The projection data recorded with the various detector rows are summed in the central processor in a manner corresponding to the associated local position. The simultaneous data acquisition via several detector rows enables, among other things, a more rapid exposure of the X-ray shadowgraph. The blurring of the image caused by this type of acquisition can be compensated by means of a deblurring filter. In the inventive X-ray computed tomography apparatus, the computer unit is thus constructed so that a sharp imaging of the shadowgraph of the patient results, even given multiple scanning.

Given a more suitable adjustment of the diaphragms, and corresponding processing of the measurement data, the multirow detector or matrix detector can be used for the simultaneous correction of scatter radiation, and thus for further increasing the image quality.

DESCRIPTION OF THE PREFERRED EMBODIMENTS

Figure 1:
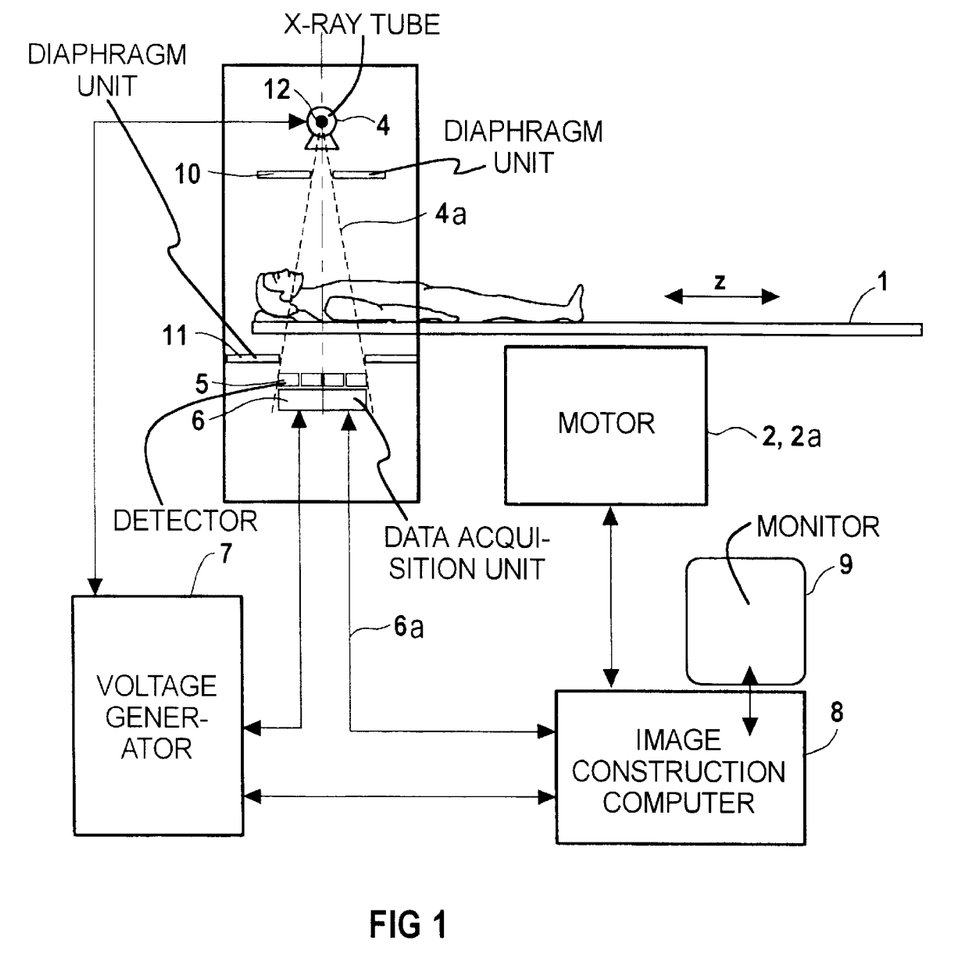
FIG. 1 shows the basic components of an X-ray computed tomography apparatus, for explaining the invention.

FIG. 1 shows the measurement arrangement of a computed tomography apparatus. Corresponding to a "third generation" system, the measurement system, which normally rotates during exposure of tomograms, is formed by the X-ray tube 4, the detector system (with a detector 5, a data acquisition unit 6 and a data transmission path 6a) and two diaphragm units 10, 11. For the exposure of a shadowgraph, the measurement system is stopped in an arbitrary position, but predominantly in the vertical (tube at top) or horizontal (tube at the side) position. The patient table 1, which is adjustable in height, can be moved back and forth by means of a motor 2 in the direction of the double arrow 3. The detector 5 is formed by several parallel detector rows (at least two), and is thus designed as a multirow detector or a matrix detector. The individual rows in the z-direction can be designed with the same width, or with different widths.

Given an arrangement of rows of different widths, it is possible, given a corresponding gradation of the widths of the individual rows, to create a virtual matrix with elements of equal width, by means of summation of the adjacent row elements. In the further discussion which follows, however, a uniform width of all rows will be assumed. If it is not possible to form the virtual matrix in the data acquisition system, then weighting functions can be introduced in the image computer 8, corresponding to the different widths of the detector rows. The invention Includes a variant, constructed In this way, of the computed tomography apparatus.

Independent of the construction of the detector system, the output of the detector is connected to a data acquisition system 6, and is connected to the image computer 8 via a data transmission path 6a. Besides processor-related circuitry for calculating the shadowgraph, the image construction computer 8 contains input means, system control units and components for image display, image archiving and image transmission into a data network. The display of the calculated shadowgraphs takes place on a monitor 9.

The X-ray tube 4 is fed by a voltage generator 7. In addition, a control apparatus 2a for the table motor 2 is provided, which is also connected to the voltage generator 7 and to the data acquisition system 6. The X-ray tube 4 emits a fan-shaped X-ray beam 4a transverse to the longitudinal direction of the patient table 1 (in the direction of the z-axis), this beam 4a striking on the detector 5. The multirow, planar detector 5 is curved around an axis that proceeds parallel to the z-axis. The curvature is normally fashioned in such a way that the axis goes through the focus 12 and the curvature describes a circle around the focus. An arbitrarily different curvature, including a flat detector, is possible.

For fading-in the X-ray beam 4a in the direction of the z-axis, at least one slot diaphragm 10 is disposed near the tube 4. For improved construction of the slice profile and for reduction of the scatter radiation, a second slot diaphragm 11 can be provided near the detector.

In the production of a computed tomogram, by means of these slot diaphragms 10, 11 the fan-shaped X-ray beam 4a is faded-in in the direction of the z-axis in such a way that it propagates perpendicular to this axis, and transirradiates one or more narrow slices of the patient. During the rotation of the measurement system around the z-axis of the system, projection data are continuously acquired, and are supplied to the image computer 8 by the data acquisition system 6, which calculates one or several transverse slice images therefrom and effects the display thereof on the monitor 9. Given simultaneous rotation of the measurement system and the translation of the patient table 1 in the z-direction, the measurement system can also be used to produce computed tomograms in a spiral operation mode.

To produce an X-ray shadowgraph, the measurement arrangement is locked against rotation. Given a simultaneous fixed position of the patient table 1, a strip-type shadowgraph having the width of the detector 5 is thus possible. If the region to be displayed exceeds, in the z-direction, the width of the detector matrix, the patient table 1 is moved relative to the measurement system in the direction of the z axis by a predetermined path, while the X-ray tube 4 is activated to emit X-rays. The detector 5 thereby continuously supplies, via the data acquisition system 6 and the transmission path 6a, measurement data in the form of measurement value projections $P_M(j, i, k)$ for the j-th projection and the i-th row of the detector 5. Within a projection, the channels are designated with k. The patient is thereby scanned several times in the z-direction by means of the parallel detector rows.

From the values $P_M(j, i, k)$ the tomogram T, or the tomograms $T_i$ allocated to the detector rows i, are produced and displayed on the monitor 9. The calculation of the tomograms is described in detail below.

By adjustment of the diaphragms 10, 11, different typical characteristics of the system for producing tomograms with an arrangement as specified above can be obtained:

a) Single-row mode

Figure 2:
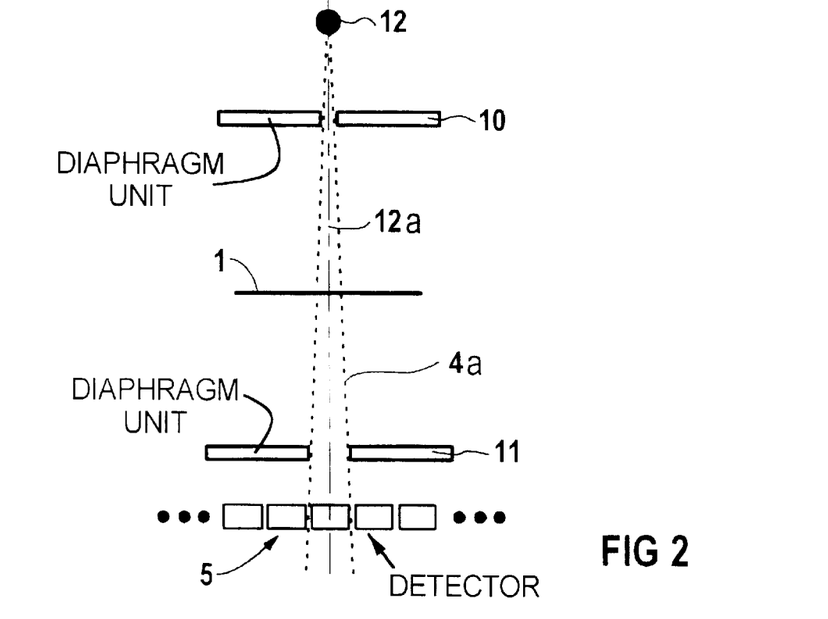
FIGS. 2, 3a, 3b, 3c and 4 respectively show the measurement arrangement of the X-ray computed tomography apparatus according to FIG. 1 at various diaphragm settings.

FIG. 2 shows that in the production of a tomogram with a detector 5 oriented symmetrically to the focus plane 12a of the focus 12 with n rows, use is made only of one detector row. The number n should thereby be odd. The slot diaphragms 10, 11 are correspondingly adjusted so that only one detector row, namely the center detector row, is struck by the X-ray beam 4a. Correspondingly, also only the measurement values of the center row are transmitted to the computer 8 by the data acquisition system 6. In terms of radiation, the situation thus achieved for the production of an X-ray shadowgraph is exactly equivalent to that using a detector constructed from a single detector row.

Figure 3A:
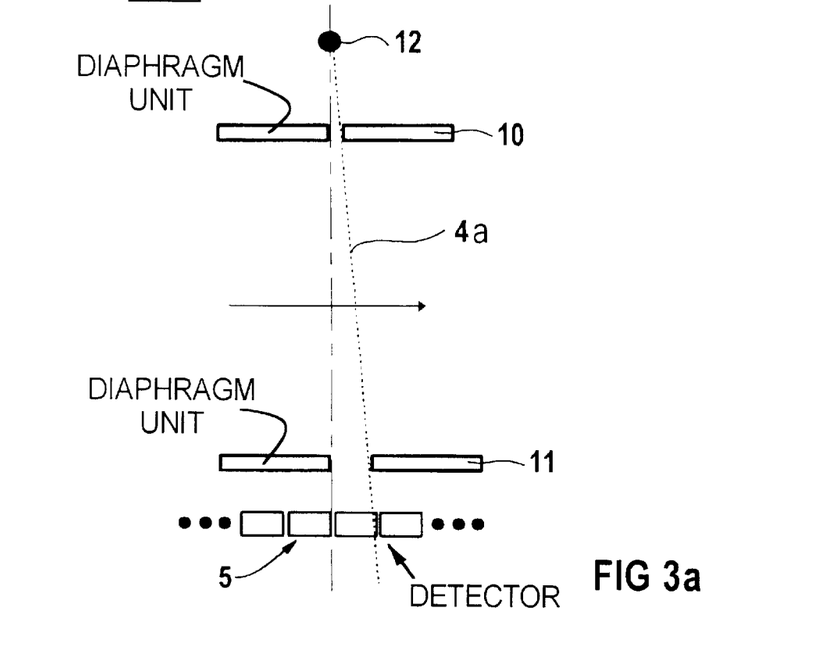
Figure 3B:
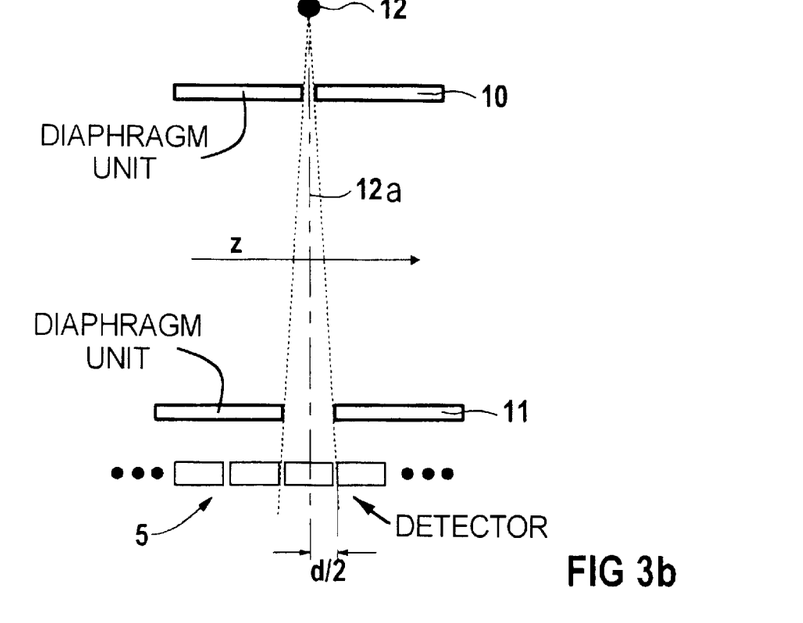

Given an even number of detector rows, i.e., if n is an even number, and a symmetrical arrangement, it is possible to adjust the slot diaphragms 10, 11 as shown in FIG. 3. Since the focus 12 according to FIG. 3a is symmetrical to the detector 5, the X-ray beam 4a is slightly oblique, given fading-in according to FIG. 3a. This oblique position can be avoided if the detector 5 is displaced slightly in the direction of the z-axis. In FIG. 3b, the detector is displaced by half the width of a detector row d/2, and is thus oriented asymmetrically to the focus plane 12a.

Figure 4:
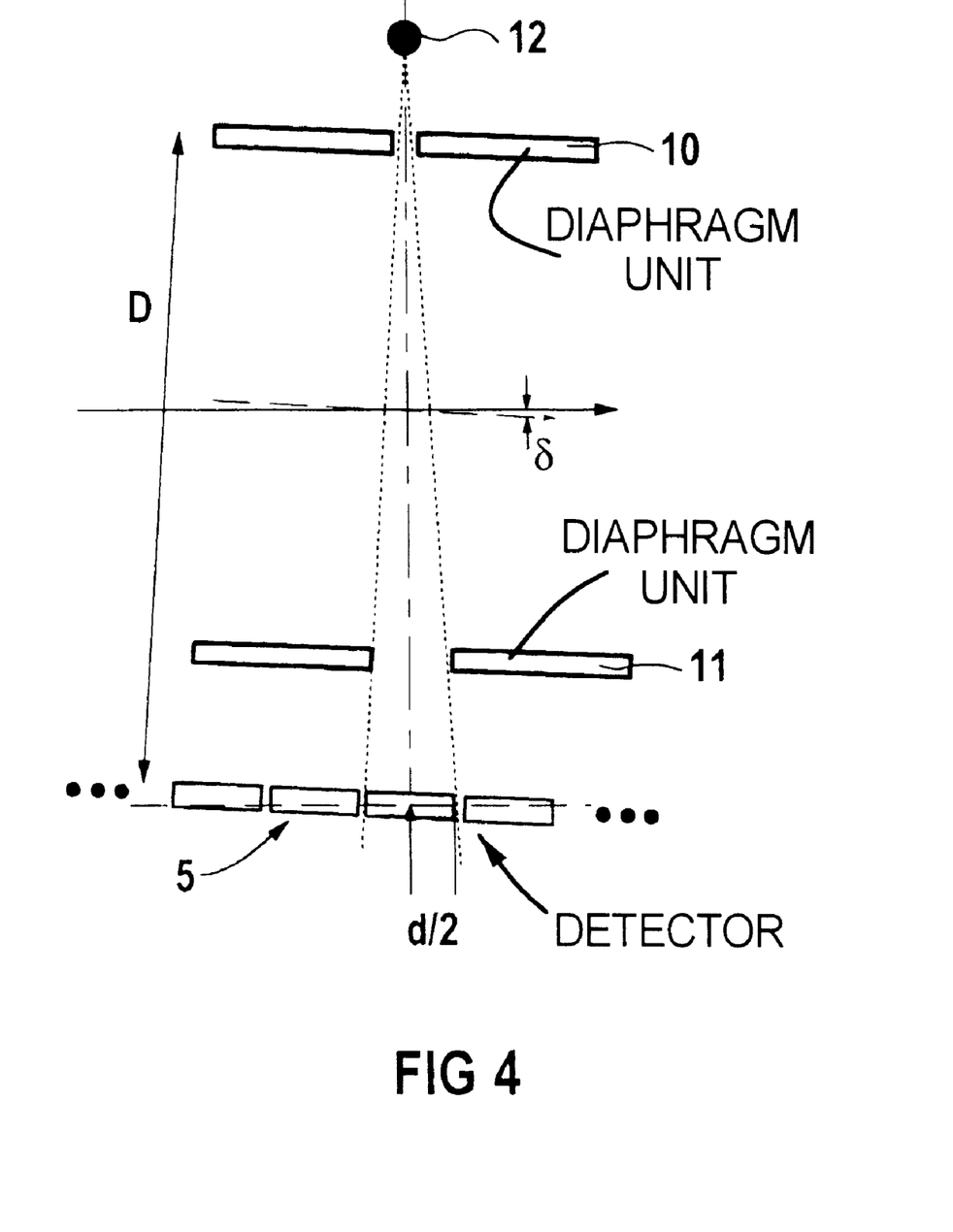

A fixed asymmetrical orientation of the detector 5 leads to an enlargement of the cone angle in the production of tomograms. By means of a slight tilting of the focus plans 12a, a shadowgraph can be constructed in a position of the tube 4 vertically above or below the patient table 1, without these disadvantages. Corresponding to FIG. 4, the tilting is thereby $$\delta = \arctan(d/2D),$$

wherein d is the width of the detector row and D is the spacing of the detector 5 from the focus 12. Thus, even with an even number of rows and a preferred tube position, a projection of the shadowgraph exactly perpendicular to the plane of the patient table is possible.

Figure 3C:
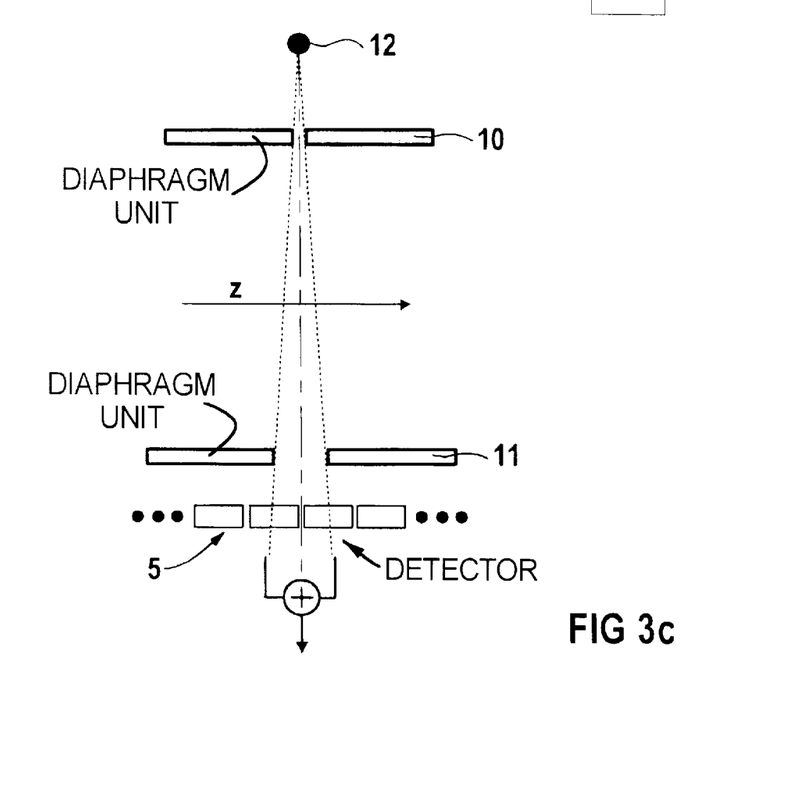

Alternatively. given an even number of rows a fading-in according to FIG. 3c is also possible. The diaphragms 10 and 11 are adjusted so that the two center rows are each half irradiated. By means of an additional addition element, the channels of the two rows can be combined directly before the A/D conversion, and thus can be supplied to the data acquisition system 6, or can be acquired separately and transmitted to the image computer 8. In the latter case, the addition of the channels of adjacent rows takes place in the image computer 8.

b) Multirow mode

Figure 5:
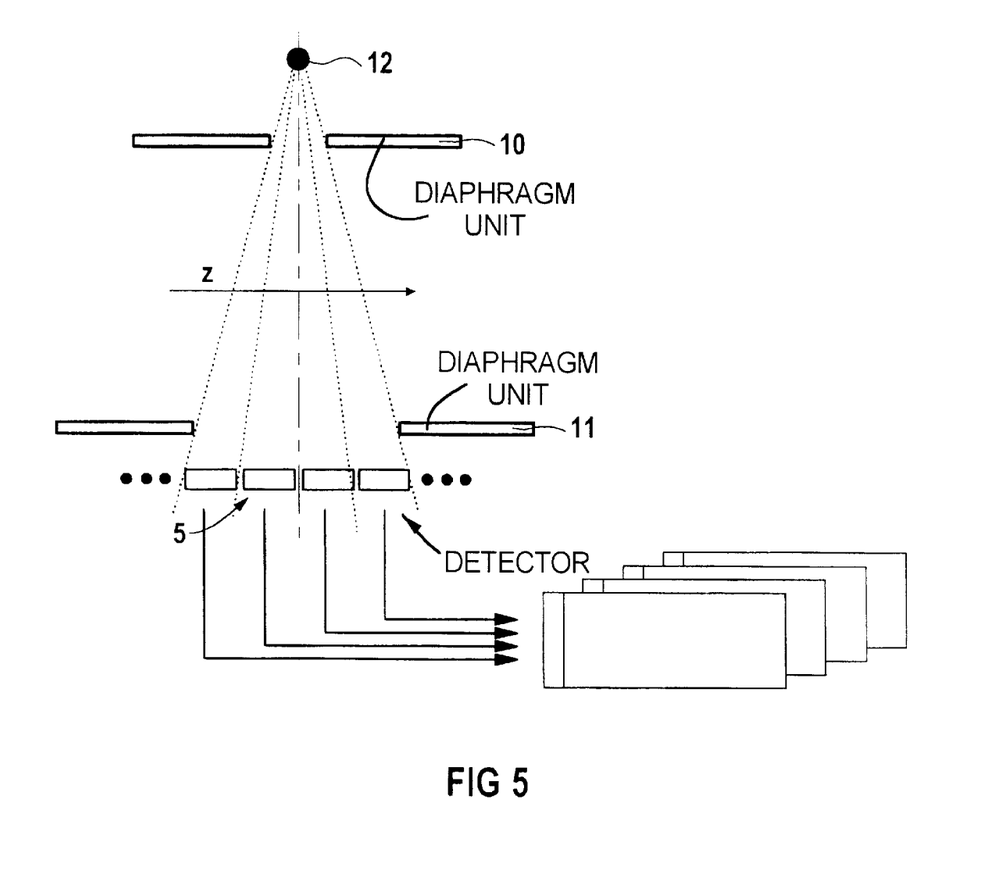
FIG. 5 shows the superposition of partial images, given simultaneous measurement with several detector rows in accordance with the invention.

FIG. 5 shows an advantageous use of the detector 5, in which, from the detector 5, m (m≦n) parallel detector rows are selected from the n rows of the multirow detector or matrix detector, by means of corresponding adjustment of the slot diaphragms 10, 11.

It is fundamentally possible with this arrangement to record with each detector row i (i=1, ... , m) the data for a separate shadowgraph $T_i$ (i=1,2,3,4 in the example of FIG. 5). The production of the individual images then takes place corresponding to the calculations for the shadowgraph in the one-row detector, by combination of several projections of the same detector row to form equidistant image lines in the shadowgraph. After the finishing of the measurement, the shadowgraphs $T_I$ and $T_{I+1}$ can be displaced relative to one another in the z direction by a distance that corresponds to the width $\Delta z_d$ of the individual slice in the isocenter of the computer tomogram, to form a summation image. By means of this displacement before the addition, the precise spatial correlation of the rows of the individual images is guaranteed.

More precisely, $Z_{iI}$ designates the I-th row in the shadowgraph $T_I$ for the detector row i. The I-th row $Z_I$ of the summation image is then composed as follows:

$$Z_l = Z_{m,1} + Z_{m-1,l+1} + Z_{m-2,l+2} + \ldots + Z_{1,l+m-1} = \sum_{i=1}^{m} Z_{i,1+m-i}$$

or, in relation to the images $T_i$:

$$T(l, k) = \sum_{l=1}^{m} T_i(l + m - l, k)$$

the index k thereby designates the image elements within the I-th row.

For the inventive summation of the information from the individual detector rows, it is thus unimportant whether partial images $T_I$ are first produced and these are then summed to form the output image, or whether the results of the individual rows are superposed already during the measurement. The Inventive method for on-line calculation of the superposition of shadowgraphs ("growing topogram") is presented below.

Deblurring Filter

By means of the simultaneous scanning of several slices lying next to one another, an acceleration of the shadowgraph recording is possible. With the more rapid displacement of the patient table necessary herefor, however, there also ensues a more pronounced blurring of the shadowgraphs in the z direction. In order to compensate for such blurring, a sharp imaging can be achieved by using a deblurring filter. The realization of a deblurring filter used in a shadowgraph is specified below.

Adaptive Scatter Radiation Correction

Besides the summation of individual shadowgraphs for better dosage use, the measurement in the multirow mode can also be constructed so that an adaptive scatter radiation correction can be carried out for image improvement.

Figure 6:
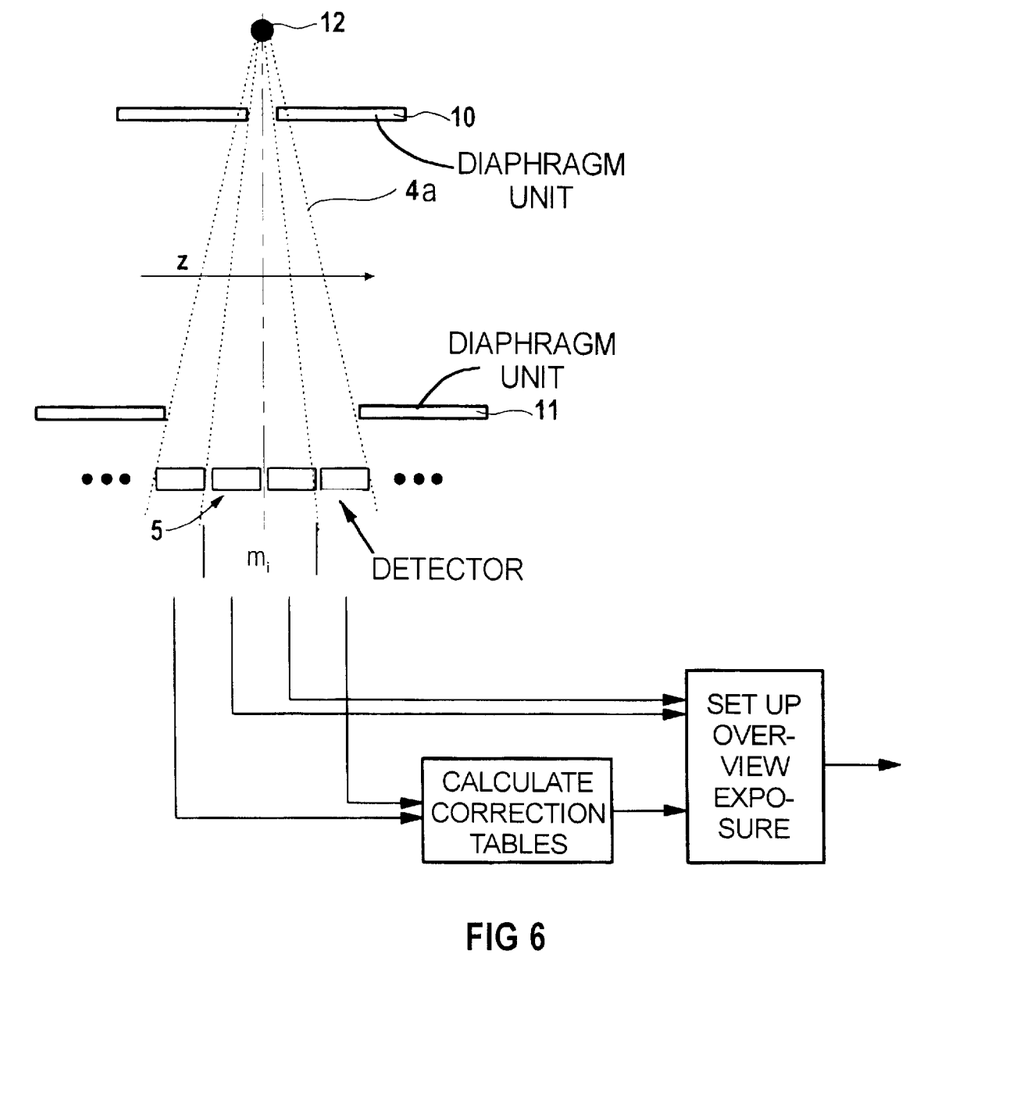
FIG. 6 shows a system for correction of scatter radiation by means of additional measurement in the shadowed region in accordance with the invention.

According to the invention, for this purpose the X-ray radiation is faded-in in the z-direction in such a way that the direct X-ray radiation strikes only a part of the detector rows. Preferably, as shown in FIG. 6, the X-rays will be oriented symmetrically to the center detector rows $m_i$. The outer detector rows (or at least one row that does not lie in the direct X-ray radiation) can then be used to measure the scatter radiation portions. Corresponding to the computing method indicated below, the information from the scatter radiation measurement is used to correct the actual measurement rows.

Advantages of this Multirow Technology:

a) Given the same tube current, the dosage is multiplied (m-fold) for a shadowgraph. This is particularly important given higher subject attenuation (obese patients, lateral shadowgraph in the shoulder region).

b) Given a comparable dose, the tube current can correspondingly be reduced by a factor of 1/mm.

c) If, given use of the marrow detector, the exposure parameters of tube current and doe per surface are hold constant, the exposure can be achieved in 1/m-th of the time, or, given identical exposure time, an m-times expansion of the shadowgraph in the z-direction can be achieved.

d) By means of the corresponding adjustment of the collimators 10, 11 and the image calculation, with the multirow system it is possible to achieve an adaptive scatter radiation correction, and thus an improvement of the imaging.

Figure 7:
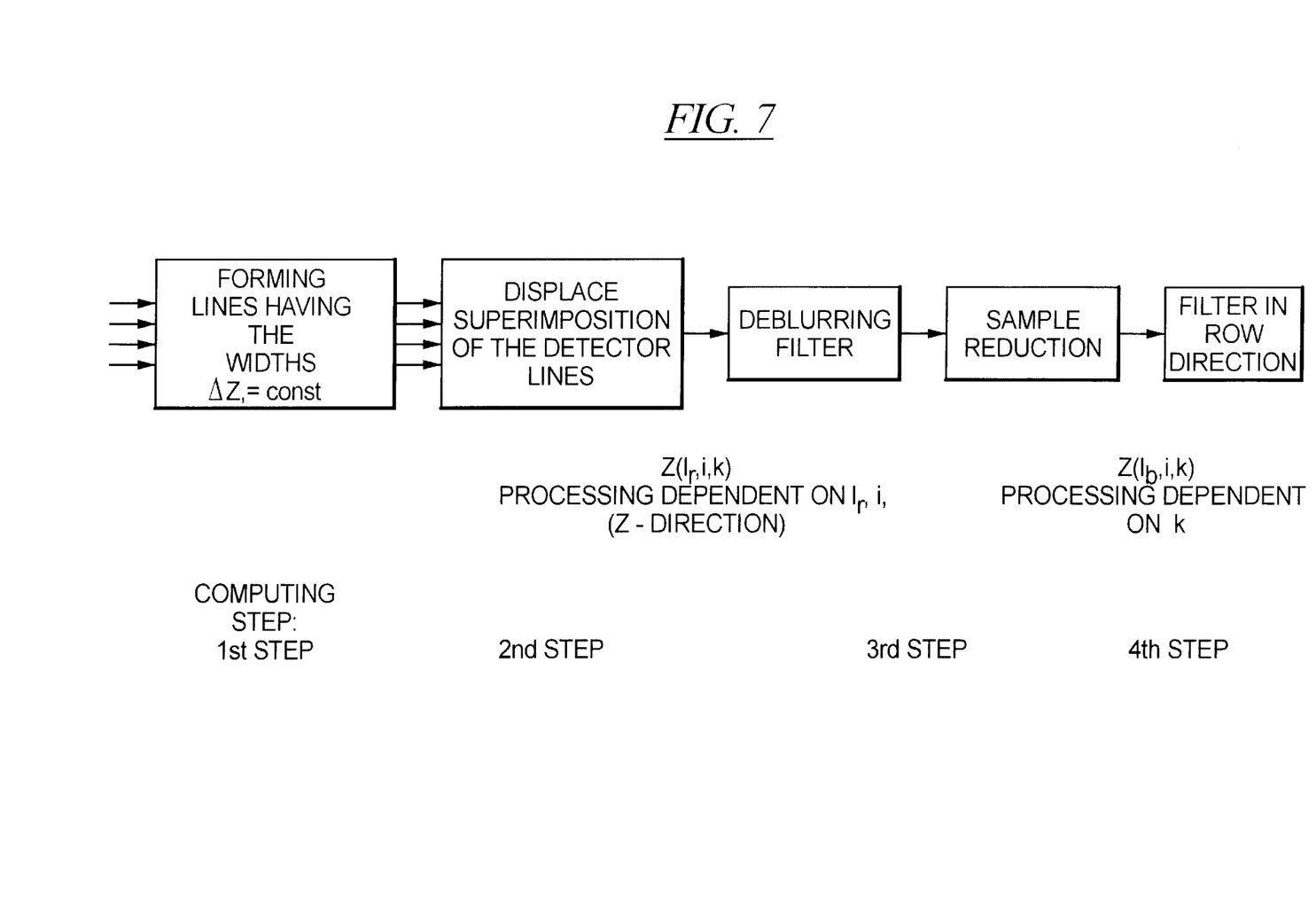
FIG. 7 shows an overview of the image construction in the shadowgraph in accordance with the invention in accordance with the invention.
Figure 8:
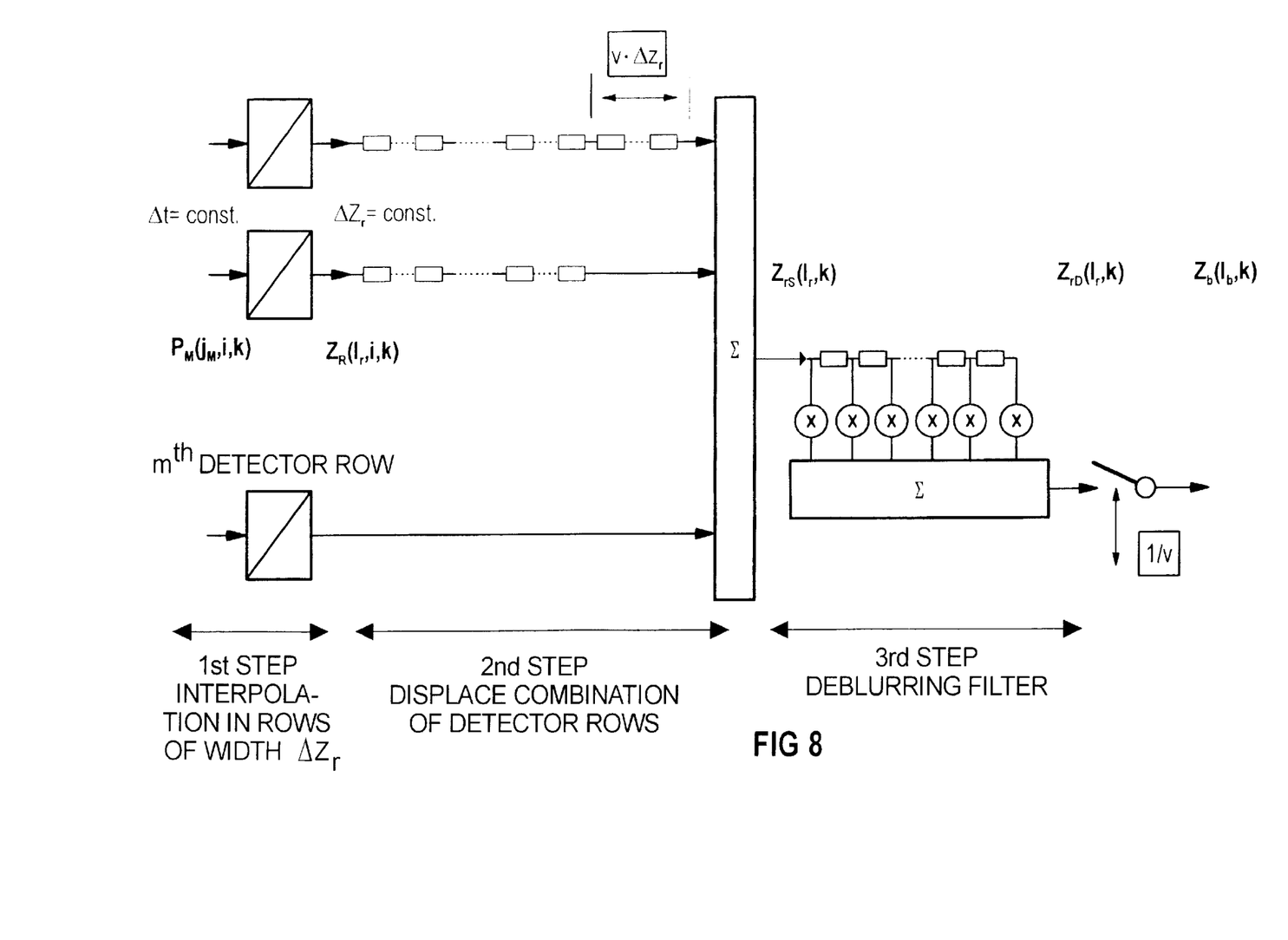
FIG. 8 shows a block circuit diagram for the combination of detector channels and for the deblurring filter in accordance with the invention.

Image Calculations for the X-ray Shadowgraph with Multirow Detectors:

Corresponding to the method specified for on-line shadowgraph calculation for single-row detectors (German OS 42 23 430, corresponding to U.S. Pat. No. 5,315,628), an on-line processing can be carried out in the image computer 8 for the multirow shadowgraph. In order to reap the full benefit of the above-described advantages of the multirow system, the new calculating methods corresponding to FIGS. 7 and 8 are shown. The calculations shown in the block images are carried out respectively for each row, keeping pace with the measurement, and the shadowgraph, as a "growing topogram," is displayed on the monitor 9 already during the measurement. FIG. 7 gives an overview of the various computing steps.

Advantageously, the algorithm allows all contributions from the various detector rows to be used directly for the on-line calculation of an image line.

For processing the projection data $P_M$, in a first computing step the projections (measured at chronologically constant intervals dt=const, of the respective i-th detector row $P_M(j, i, k)$), are converted by means of a weighted summation (interpolation) to form image lines $I_r$ of the respective i-th detector row $Z_r(I_r, i, k)$, with a constant spacing $\Delta z_r$=const (see FIG. 8). The number L of the summed projections $P_M$ per row $Z_r$ is thereby a function of the instantaneous speed $v_{jM}$ of the movement of the table 1. For optimization of the deblurring filter, it is useful first to assume an Image scanning frequency in the z-direction that is increased by a factor v. The line spacing for the calculation is thus $$\Delta z_r = \Delta z_b/v$$

wherein $\Delta z_b$ designates the spacing of the lines in the final shadowgraph. Expressed as an equation, there results:

$$Z_r(l_r, i, k) = \frac{1}{L} \sum_{\Delta z_i} P_M(j_M, i, k)$$

with $$\Delta z_p = \sum_{jM} \Delta t \cdot v_{jM}$$

In a second step, the contributions of the various detector rows are combined. Given detectors with identical row spacings, or projections already combined to form identical row spacings, then, corresponding to the offset of $\Delta z_b = / v \cdot \Delta z_r$, respective adjacent detector rows (index k) are summed from packets offset by v rows (index $I_r$):

$$Z_{rS}(l_r, k) = \frac{1}{m} \sum_{k=1}^{m} Z_r(l_r + (m-\kappa)v, \kappa, k)$$

If the detector rows are present in a non-equidistant grid, then interpolation must take place in a suitable way for each channel k between the adjacent detector rows i and i+1 and the successively read-out values . . . , $I_r-1$, $I_r$, $I_r+1$, . . . of the individual detector rows. The interpolations, respectively having n support points between the successive values and each two adjacent rows, can be combined to form an n-m interpolation matrix. With the interpolation weights $b(\lambda, K)$, which are to be determined dependent on the type of interpolation used, the following general interpolation prescription can be indicated for the second processing step:

$$Z_{rS}(l_r, k) = \sum_{\lambda=-n/2}^{n/2} \sum_{k=1}^{m} b(\lambda, \kappa) Z_r(l_r + \lambda + (m-\kappa)v, \kappa, k)$$

In a third step, the combination of the detector rows follows the actual deblurring filter for the reduction of blurring artefacts due to the continuous movement of the patient table I. Methods for determining the parameters of the filter are indicated in the literature, among others in x)

Preferably, the deblurring filter is constructed as a non-recursive digital filter (FIR-filter). The length M (M being odd) of the impulse response, and the coefficients h(K) thereof, are determined corresponding to the rounding in the z-direction. The output values $Z_{rD}(I_r, k)$ of the filter are calculated corresponding to the relation:

$$Z_{rD}(l_r, k) = \sum_{\kappa=-n/2}^{n/2} Z_{rS}(l_r - \kappa, k) \cdot h(\kappa)$$

For the execution of the deblurring filter, a scanning increased by v in the z-direction is chosen. By means of corresponding subscanning of the output values, the actual image lines $Z_b(I_b, k)$ are obtained:

$$Z_b(l_b, k) = Z_{rD}(v \cdot l_b, k)$$

The exemplary realization shown in FIG. 8 is a possible embodiment. For optimization of the computing sequences, variant reaizations of the relations stated above are included in the invention. Specifically, the deblurring filter can be constructed so that the values that are not required in the subscanning do not have to be calculated.

*) H. C. Andrews and B. R. Hunt, Digital Image Restoration, Prentice-Hall, 1977, Chapters 4 und 5. Since all adjacent values in the grid $\Delta z_r$ contribute to the calculation of the output values $Z_{rD}$ dependent on $I_r$, all measured data are acquired. No additional influence on the image noise or the "dosage usage" occurs due to the subscanning.

The calculations in steps one to three are carried out for all elements k in the various rows. A parallel processing of the elements k is thereby possible given suitable structuring of the intermediate memory on several CPUs.

In a fourth computing step shown in FIG. 7, there occurs a convolution in the row direction, i.e., perpendicular to the z-direction just as in the calculation of the shadowgraph in the single-row detector. The impulse response of the filter in the row direction is selected so that an attenuation compensation and edge enhancement takes place. Care must be taken, however, to achieve an image impression that is homogenous In both directions with respect to the quantum noise. The filtering in the row direction can be executed as direct convolution or as "fast convolution" by means of fast Fourier transformation.

Figure 9:
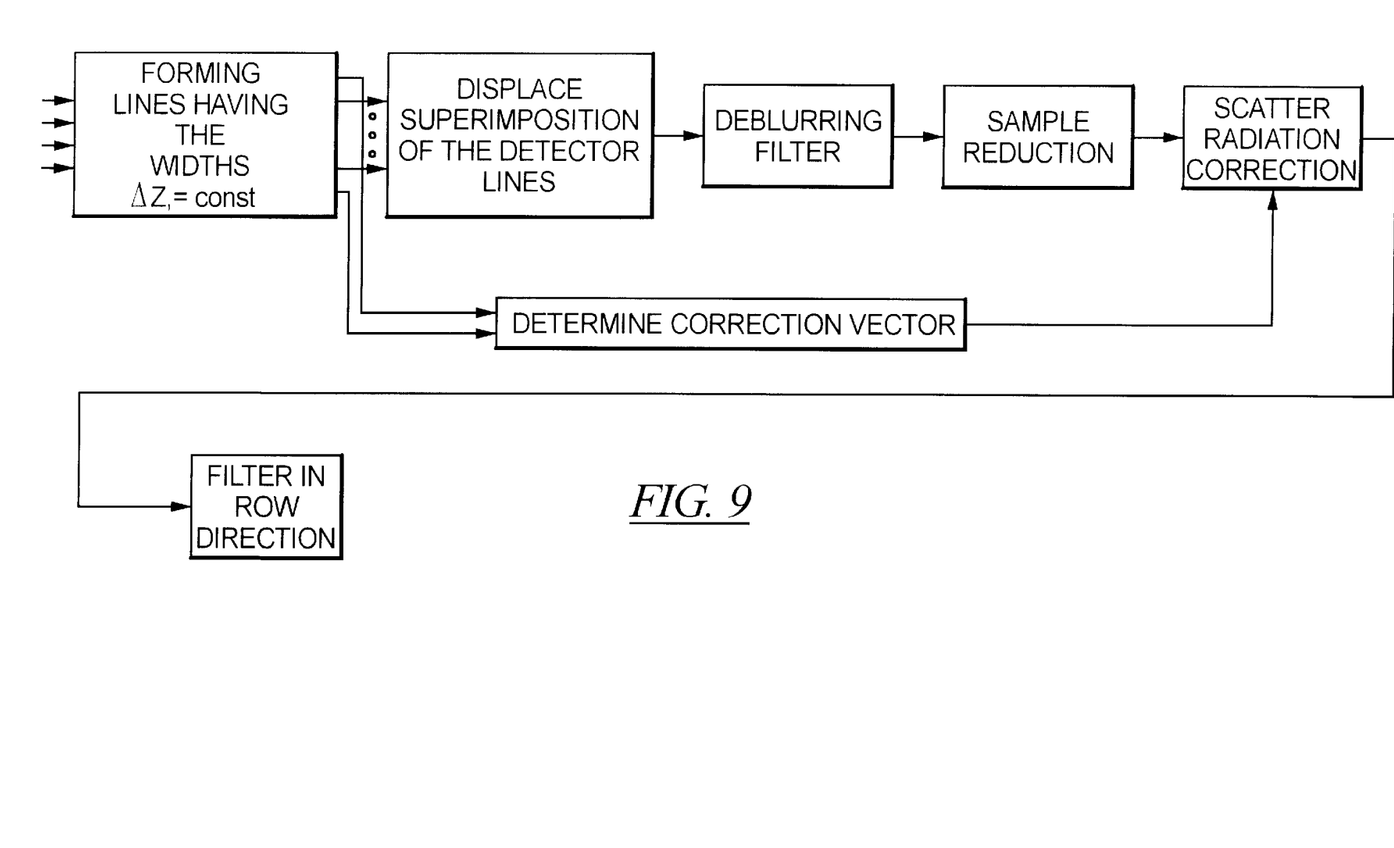
FIG. 9 shows an overview for the method for a correction of the scatter radiation in accordance with the invention.

The shading in of the beam 4a can be carried out in such a way that, as described above, an adaptive scatter radiation correction is possible. For the actual image construction, only the inner $m_i$ detector rows are then used. From the measurement values of the outer detector rows, the object-dependent scatter radiation influences on the inner detector rows can be determined, and a correction matrix S(i,k) can be formed for the individual detector rows that contribute to the image construction. For simpler calculation, in many cases a combination of the correction matrix S(i,k) to form a correction vector S'(k) is possible. The scatter radiation correction can then take place according to the scanning reduction:

$$Z_{rS'}(l_b, k) = F[Z_r(l_b, k) jS(k)]$$

The corrected values $Z_{rS'}(I_b, k)$ are then supplied to the last computing step for convolution in the row direction, as shown in FIG. 9.

The execution of the individual computing steps can be executed in separate, dedicated computing or processing circuits respectively corresponding to the blocks in FIGS. 7, 8 and 9. The inventive method can also be carried out in one or more programmable computing stages.

x) Although various minor modifications might be suggested by those skilled in the art, it should be understood that our wish to embody within the scope of the patent warranted hereon all such modifications as reasonably and properly come with the scope of our contribution to the art.

x) The invention was explained on the basis of a "third generation" system. The invention can, however, also be used in connection with "fourth generation" systems, which have a rotating X-ray tube and a non-rotating, ring shaped detector.

We claim as our invention:

1. An X-ray computed tomography apparatus comprising:
   an X-ray source which emits an X-ray beam;
   a radiation detector comprising a plurality of detector rows, said detector being disposed so that said X-ray beam is at least partially incident thereon;
   a first slot diaphragm disposed proximate said X-ray source in a path of said X-ray beam;
   a second slot diaphragm disposed proximate said radiation detector in said path of said X-ray beam;
   means for rotating said X-ray source around an examination subject for obtaining tomographic data;
   a computer connected respectively to said detector rows by a plurality of lines, supplied with said tomographic data, for producing a computed tomogram from said tomographic data;
   means for temporarily maintaining said X-ray source and said detector in a non-rotating position;
   a movable patient table adapted to receive an examination subject thereon;

means for producing relative non-rotational motion between said table and said X-ray source and said radiation detector when said X-ray source and said radiation detector are maintained in said non-rotating position;

means, during said relative motion, for individually adjusting said first and second slot diaphragms for causing said X-ray beam to be incident on a selected number of said rows of said detector to produce shadowgraphic data; and said shadowgraphic data from said detector rows being supplied separately and individually to said computer via said plurality of lines, and said computer comprising means for producing a shadowgraph from said shadowgraphic data from a selected number of said detector rows.

2. An X-ray computed tomography apparatus as claimed in claim 1 wherein said means for individually controlling said first and second slot diaphragms comprises means for using only one of said detector rows for producing said shadowgraphic data.

3. An X-ray computed tomography apparatus as claimed in claim 1 wherein said radiation detector comprises an odd number of said detector rows, including a central detector row, and wherein said means for individually adjusting said first and second slot diaphragms comprises means or symmetrically positioning said X-ray beam relative to said central detector row for producing said shadowgraphic data.

4. An X-ray computed tomography apparatus as claimed in claim 1 wherein said X-ray beam, when said X-ray source and said radiation detector are maintained in said non-rotating position, has a focus plane associated therewith, and wherein said radiation detector comprises an even number of said detector rows, and wherein said means for individually adjusting said first and second slot diaphragms comprises means for selecting a single one of said detector rows which is asymmetrical to said focus plane for producing said shadowgraphic data.

5. An X-ray computed tomography apparatus as claimed in claim 1 wherein said X-ray beam, when said X-ray source and said radiation detector are maintained in said non-rotating position, has a focus plane associated therewith, and wherein said radiation detector is disposed relative to said focus plane displaced in a direction perpendicular to said focus plane by half a width of a detector row.

6. An X-ray computed tomography apparatus as claimed in claim 1 wherein said X-ray beam, when said X-ray source and said radiation detector are maintained in said non-rotating position, has a focus plane associated therewith, and further comprising means for moving said radiation detector in a direction substantially perpendicular to said focus plane.

7. An X-ray computed tomograph apparatus as claimed in claim 1 wherein said radiation detector comprises an even number of said detector rows, including two center rows, and wherein said means for adjusting said first and second slot diaphragms comprises means for causing said X-ray beam to be incident on said two center rows for producing said shadowgraphic data.

8. An X-ray computed tomography apparatus as claimed in claim 7 wherein said means for adjusting said first and second slot diaphragms comprises means for causing said first and second slot diaphragms to partially occlude two center detector rows, wherein each of said center detector rows generates an output electrical signal dependent on X-rays respectively incident thereon, and further comprising means for summing said output signals from said center detector rows, partially occluded by said first and second slot diaphragms, for producing a detector signal representing a radiation detector width which is smaller than said two center detector rows.

9. An X-ray computed tomography apparatus as claimed in claim 8 wherein said means for adjusting said first and second slot diaphragms comprises means for occluding said two center detector rows to produce a detector signal for a detector width which is equal to a width of a single one of said detector rows.

10. An X-ray computed tomography apparatus as claimed in claim 8 wherein said means for summing is contained in a data acquisition system, which is separate from said computer.

11. An X-ray computed tomography apparatus as claimed in claim 8 wherein said means for summing is contained in said computer.

12. An X-ray computed tomography apparatus as claimed in claim 1 wherein said radiation detector comprises an even number of said detector rows, wherein said X-ray beam, when said X-ray source and said radiation detector are maintained in said non-rotating position, has a focus plane associated therewith, wherein said means for adjusting said first and second slot diaphragms comprises means for causing said X-ray beam to strike one of said detector rows which is asymmetrical to said focus plane for producing said shadowgraphic data, and further comprising means for causing said X-ray beam to be tilted by an angle for causing a measurement plane to be perpendicular to said table.

13. An X-ray computed tomography apparatus as claimed in claim 1 wherein said X-ray beam, when said X-ray source and said radiation detector are maintained in said non-rotating position, has a focus plane associated therewith, and wherein said means for adjusting said first and second slot diaphragms comprises means for causing said X-ray beam to simultaneously strike a plurality of said detector rows, each detector row being struck by said X-ray beam having an offset relative to said focus plane and each of said detector rows struck by said X-rays producing an electrical signal dependent on X-rays incident thereon, and further comprising means for summing said electrical signals of the respective detector rows which are struck by said X-rays, dependent on the respective offsets of said detector rows which are struck by said X-rays.

14. An X-ray computed tomography apparatus as claimed in claim 13 wherein said means for summing said electrical signals dependent on the respective offsets of said detector rows which are struck by said X-rays comprises means for calculating an offset for each detector row which is struck by said X-rays dependent on respective slice thicknesses in an isocenter of said computed tomography apparatus.

15. An X-ray computed tomography apparatus as claimed in claim 13 wherein said means for summing comprises means for calculating a shadowgraph individually for each of said detector rows which is struck by said X-rays, and for summing the respective shadowgraphs from the individual detector rows dependent on the respective offset of the detector rows.

16. An X-ray computed tomography apparatus as claimed in claim 13 wherein all of the detector rows which are struck by said X-rays are of equal width and wherein said means for summing comprises means for summing said electrical signals row-by-row dependent on the respective offsets as said electrical signals are produced by said detector rows struck by said X-rays.

17. An X-ray computed tomography apparatus as claimed in claim 16 wherein said means for producing a tomogram comprises means for producing a shadowgraph as a patient on said table is advanced through said X-ray beam in an advancement direction at a first scan rate in said advancement direction, and wherein said means for summing includes means for acquiring said electrical signals from said detector rows which are struck by said X-rays at a second scan rate in said advancement direction, said second scan rate being higher than said first scan rate.

18. An X-ray computed tomography apparatus as claimed in claim 13 wherein said detector rows which are struck by said X-rays have respectively different widths, and wherein said means for summing comprises means for directly processing and interpolating said electrical signals as said detector rows are struck by said X-rays, including summing said electrical signals dependent on the respective offsets and interpolating said electrical signals to normalize said electrical signals as if said detector row struck by said X-rays were all of equal widths.

19. An X-ray computed tomography apparatus as claimed in claim 18 wherein said means for producing a tomogram comprises means for producing a shadowgraph as a patient on said table is advanced through said X-ray beam in an advancement direction at a first scan rate in said advancement direction, and wherein said means for summing includes means for acquiring said electrical signals from said detector rows which are struck by said X-rays at a second scan rate in said advancement direction, said second scan rate being higher than said first scan rate.

20. An X-ray computed tomography apparatus as claimed in claim 13 comprising means for advancing said table through said X-ray beam in an advancement direction during production of said shadowgraphic data, and further comprising deblurring filtering means for acting on said shadowgraphic data for compensating for blurring due to motion of said table in said advancement direction.

21. An X-ray computed tomography apparatus as claimed in claim 20 wherein said means for adjusting said first and second slot diaphragms comprises means for causing said X-ray beam to be incident on a plurality of said detector rows for producing said shadowgraphic data, each detector row struck by said X-ray beam generating an electrical signal corresponding to X-rays incident thereon, and further comprising means for summing said electrical signals to produce said shadowgraphic data, and wherein said deblurring filter means is supplied with said shadowgraphic data directly after summing of said electrical signals while said detector rows are struck by said X-ray beam.

22. An X-ray computed tomography apparatus as claimed in claim 20 wherein said deblurring filter means comprises means for acting on said shadowgraphic data with a plurality of filter coefficients adapted to an instantaneous advancement speed of said table in said advancement direction.

23. An X-ray computed tomography apparatus as claimed in claim 20 wherein said means for producing a shadowgraphic image comprises means for producing a shadowgraphic image at a final line frequency, and further comprising scan reduction means for reducing a line frequency of said shadowgraphic data from a frequency greater than said final line frequency.

24. An X-ray computed tomography apparatus as claimed in claim 20 wherein said final shadowgraph comprises a plurality of image lines, and wherein said deblurring filter means comprises means for acting only on shadowgraphic data which is used to produce said lines in said final shadowgraph.

25. An X-ray computed tomography apparatus as claimed in claim 1 further comprising means for using at least one of said plurality of detector rows for measuring scatter radiation associated with said X-ray beam.

26. An X-ray computed tomography apparatus as claimed in claim 25 further comprising means for compensating for said scatter radiation, as measured by said means for measuring scatter radiation, in said shadowgraph.

27. An X-ray computed tomography apparatus as claimed in claim 1 comprising means for advancing said table through said X-ray beam in an advancement direction during production of said shadowgraphic data, and further comprising means for high-pass filtering said shadowgraphic data in a direction transverse to said advancement direction.

28. An X-ray computed tomography apparatus as claimed in claim 1 comprising means for advancing said table through said X-ray beam during production of said shadowgraphic data and comprising means for obtaining a plurality of projections, at time constant intervals during the advancement, and for converting said projections into image lines of constant width corresponding to an instantaneous table speed, for processing in said computer.

* * * * *